(12) United States Patent
Simmons et al.

(10) Patent No.: US 6,629,967 B1
(45) Date of Patent: Oct. 7, 2003

(54) LONGITUDINAL PUCKERED-EDGE LIQUID BARRIERS FOR ABSORBENT ARTICLES

(75) Inventors: Eva Simmons, Mölndal (SE); Peter Rönnberg, Mölndal (SE); Anders Gustafsson, Billdal (SE)

(73) Assignee: SCA Hygiene Products AB, Göteborg (SE)

( * ) Notice: Subject to any disclaimer, the term of this patent is extended or adjusted under 35 U.S.C. 154(b) by 0 days.

(21) Appl. No.: 09/380,209
(22) PCT Filed: Feb. 25, 1998
(86) PCT No.: PCT/SE98/00340
§ 371 (c)(1),
(2), (4) Date: Nov. 8, 1999
(87) PCT Pub. No.: WO98/37842
PCT Pub. Date: Sep. 3, 1998

(30) Foreign Application Priority Data

Feb. 26, 1997 (SE) ............................................. 9700697

(51) Int. Cl.[7] .................................................. A61F 13/20
(52) U.S. Cl. .................................... 604/385.27; 604/387
(58) Field of Search ...................... 604/385.01, 385.24, 604/385.27, 385.28, 385.25, 385.26, 386, 387

(56) References Cited

U.S. PATENT DOCUMENTS 4,324,246 A * 4/1982 Mullane et al. ............. 128/287
5,445,627 A   8/1995 Mizutani et al. ......... 604/385.2
5,746,732 A * 5/1998 Olsson et al. ............ 604/385.2

FOREIGN PATENT DOCUMENTS

| EP | 0 264 238 | 4/1988 | |
|---|---|---|---|
| EP | 0 534 488 | 3/1993 | |
| EP | 0 745 367 | 12/1996 | |
| GB | 2 188 532 | 10/1987 | |
| NO | 0264238 | 10/1987 | |
| WO | 93/19711 | * 10/1993 | ........... A61F/13/15 |

* cited by examiner

Primary Examiner—Weilun Lo
Assistant Examiner—Michele Kidwell
(74) Attorney, Agent, or Firm—Burns Doane Swecker & Mathis LLP

(57) ABSTRACT

An absorbent article includes a liquid-permeable upper sheet, a liquid impermeable bottom sheet, and an absorbent body between the bottom sheet and the upper sheet, and at least one longitudinally extending liquid barrier comprising an elongated elastic element and an elongated, essentially liquid-impermeable and inelastic material on each side of a longitudinal center line. A liquid impermeable top sheet with an aperture intended to lie in register with a wearer's anus and urethral orifice may also be included. A prestretched elastic band is attached to either an edge of an inelastic material of the liquid impermeable barrier or to the aperture-defining edge of the liquid permeable top sheet. When the article is donned, the elastic device will lie against a wearer, with a free part facing toward the longitudinal center line and a stretchable, puckered sealing edge facing outward from the longitudinal center line.

19 Claims, 4 Drawing Sheets

Prior Art FIG. 2a

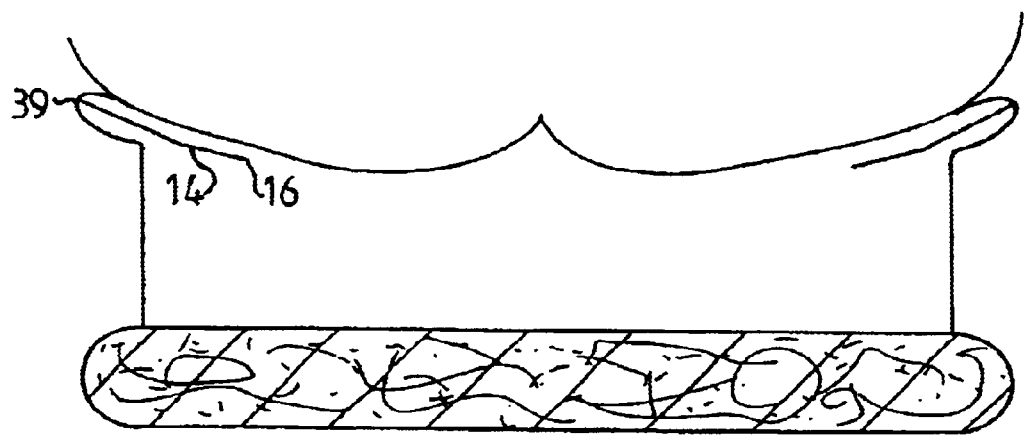
FIG. 3a
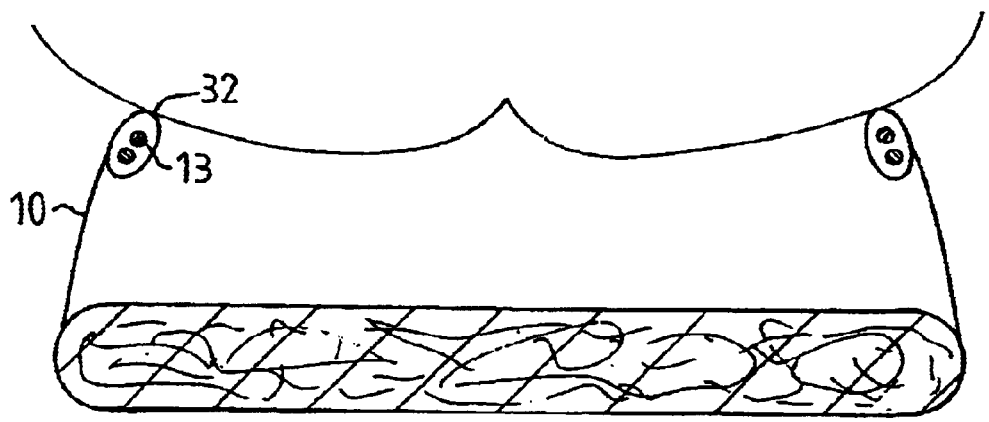
Prior Art    FIG. 3b

LONGITUDINAL PUCKERED-EDGE LIQUID BARRIERS FOR ABSORBENT ARTICLES

BACKGROUND

The present invention relates to an absorbent article that includes an effective liquid barrier, an element that can be used as a liquid barrier in an absorbent article, and a method of producing liquid barriers in absorbent articles.

An absorbent article includes, among other things, a bottom liquid-impermeable sheet, an absorbent layer or sheet disposed on said bottom sheet, and a top surface sheet which is intended to lie proximal to the wearer in use. When the absorbent article is a diaper or an incontinence guard, it will also include flexible side-flaps which extend laterally beyond the absorbent body on opposite sides thereof and elastic devices that extend longitudinally along the free side-edges of the side flaps at least within that part which is intended to form the crotch part of the article in use, said flaps and elastic devices enabling the absorbent article to be fitted to the wearer. The elastic devices function as leg elastic when the article is worn and are intended to seal around the wearer's thighs and also to shape the article. The flexible side-flaps form tightening or sealing edges and have the additional function of preventing liquid, and possibly faeces, from leaking out at the edges, in other words they form barriers.

As an added safeguard against the leakage of liquid from the side-edges of an article, a number of absorbent articles also include additional, inner liquid-barriers or cuffs fastened in the proximity of the longitudinal edges of the article concerned. The purpose of the liquid barrier is to prevent liquid from escaping at the edges of the absorbent article and also possibly to prevent the escape of solids, such as faeces. This second barrier is placed inwardly of the leg elastic, i.e. inwardly of the outer liquid barrier, and is comprised of an essentially liquid-impermeable material, for instance a non-woven material, and also of elastic devices which gather together, or pucker, the edge of the liquid barrier in abutment with the wearer. The unresilient, inelastic material is secured along one longitudinally extending edge thereof to the absorbent article near or at the longitudinally extending edges. The elastic device, e.g. elastic thread, is fastened along the other edge of the inelastic material, so as to gather together the liquid carrier and form a puckered edge which is partially extended or stretched when the article is donned. The puckered edge is usually formed by folding the inelastic material around one or more elastic threads, into a channel along the edge of the material. The inelastic material is glued or welded around the elastic threads. When the absorbent article is donned, the puckered edge lifts and is partially stretched, the extent of this stretch being dependent on the size of the wearer. Examples of diapers that include liquid barriers are found in SE-T3-0 264 238 and GB-A-2 188 532, for instance.

In the case of diapers that include liquid barriers or cuffs for instance, the barrier will be positioned so as to lie against the crotch and buttocks of the wearer and should prevent leakage in these areas. Each urine discharge will deliver a certain volume of liquid to the article. Because of the delay before this urine is able to penetrate through the upper sheet and be absorbed in the absorbent layer, a certain amount of urine will "float" in the absorbent article on top of the surface sheet. The barrier is intended to prevent this volume of urine from forcing its way out at the edges of the absorbent article. Cuffs can also be used on sanitary napkins, for instance.

It has been found, however, that this barrier is not leakage-proof.

The object of the present invention is to provide an improved liquid barrier that includes a more effective sealing edge and, at the same time, a softer and more comfortable edge in abutment with the wearer. A further object of the invention is to provide an absorbent article that includes at least one such barrier.

SUMMARY OF THE INVENTION

The invention relates to an absorbent article, such as a diaper, sanitary napkin, incontinence guard or like article, that includes longitudinally extending and transversely extending edges, a bottom liquid-impermeable sheet, an absorbent sheet or layer, a top liquid-permeable sheet which is intended to lie proximal to a wearer in use, and on each side of the centre line of the top sheet at least one longitudinally extending liquid barrier which is comprised of a longitudinally extending, essentially inelastic and essentially liquid-impermeable material that has two longitudinally extending edges, of which the first edge is fastened to the top liquid-permeable sheet or to the bottom liquid-impermeable sheet of the absorbent article along or adjacent to the longitudinal edge of said article, and the other edge of which is fastened to an elongated, prestretched elastic element to form a puckered, stretchable barrier edge that is intended to lie against the wearer of the article, wherein the elastic element is comprised of a band-like or ribbon-like elastic device or means having a first and a second longitudinally extending edge of which at least the first edge is fastened in a stretched state to the second edge of the essentially inelastic material such that the mutually joined edges will form a stretchable puckered first barrier edge, and including a longitudinally extending free part that forms a stretchable, essentially smooth second barrier edge, the elastic device being fastened to the essentially inelastic material in a manner such that when the article is donned said elastic device will lie against the wearer with the free part facing towards the centre line of the article and the gathered barrier edge facing outwards from the centre line of said article.

The invention also relates to an absorbent article which includes a liquid-impermeable sheet that is intended to lie against a wearer and is provided with elastic for shaping the article to the wearer's body, said sheet including an aperture which is intended to be caused to register with the anus and urethra orifice of the wearer and around which aperture a stretchable sealing edge is disposed in the essentially liquid-impermeable sheet, which edge has been puckered by a prestretched elastic element, an absorbent body being disposed on that side of the essentially liquid-impermeable sheet that lies distal to the wearer in use, the absorbent body being enclosed between a liquid-permeable sheet on that side which lies proximal to the wearer in use, and a liquid-impermeable sheet, the elastic element being comprised of a band-like elastic device having a first and a second longitudinally extending edge of which at least the first edge is fastened in a prestretched state to the essentially liquid-impermeable sheet in the sealing edge such that the puckered edges form a stretchable, puckered first barrier edge, and including a longitudinally extending free edge which forms a stretchable, essentially smooth second barrier edge, the elastic device being fastened to the liquidimpermeable sheet such that when the article is donned, the elastic device will lie against the wearer with said free part facing inwardly towards said aperture and with the gathered barrier edge facing outwardly from said aperture.

The invention also relates to a web-like element for use as a liquid barrier in an absorbent article, said element including an elongated, essentially inelastic and essentially liquid-impermeable material having two longitudinally extending edges of which the first edge is free and intended to be fastened to the absorbent article and the second edge is fastened to an elongated, stretched elastic element so as to form a puckered, stretchable barrier edge, the elastic element being comprised of a band-like elastic device having a first and a second longitudinally extending edge of which at least the first edge is fastened in a stretched state to the second edge of the essentially inelastic material such that the mutually joined edges will form a stretchable, puckered first barrier edge, and including a longitudinally extending free part that forms a stretchable, essentially smooth second barrier edge. Thus, the web-like element comprises three barrier edges, i.e. the stretchable, puckered first barrier edge, the stretchable, essentially smooth second barrier edge and a third barrier edge consisting of the first edge of the essentially inelastic and essentially liquid-impermeable material, where the first and second barrier edges in a relaxed state are shorter than the third edge and can be stretched to the length of said third edge.

When the barrier element is stretched, e.g. when an absorbent article including such an element is donned, the two stretchable barrier edges will lie generally at right angles to the inelastic material, so that the barrier element obtains a T-shape.

The second edge of the elastic device conveniently forms said free part. However, the elastic device may be folded lengthwise and the first and second edges both fastened to the second edge of the inelastic material. The folded edge of the elastic device will then form said free part.

The second edge of the elongated, inelastic material is preferably folded to form a channel around at least the stretched first edge of the elastic device. The channel is fastened to the elastic device, e.g. glued or welded thereto, and forms the puckered barrier edge. It is also possible to insert and fasten both edges of the elastic device in said channel.

Nonwoven material, e.g. a multi-layer nonwoven material, is an example of the essentially inelastic material that can be used. Such a material may be an SMS material, i.e. spunbond-meltblown-spunbond.

The elastic device may comprise elastic film or elastic ribbon based on styrene block copolymers, such as SBS (styrene-butadien-styrene), SIS (styrene-isoprenestyrene), SEBS (styrene-ethylene-butylene-styrene) or SEPS (styrene-ethylenepropylene-styrene). The film may consist of several layers and may, for instance, be a three-ply film where the outer layers consist of polypropylene. The polypropylene functions to facilitate fastening of the film to the inelastic material and may, e.g., facilitate gluing to the other material. Polypropylene also feels more comfortable to the skin than a number of other elastic films, which feel like plastic against the skin, which one wishes to avoid. Elastic nonwoven material may also be used as the elastic devices.

An inventive barrier element is produced by laying the band-like elastic device against the web-like, essentially inelastic and essentially liquid-impermeable material with its first edge stretched and parallel with and close to the second edge of the inelastic material and with its second edge facing towards the first edge of said inelastic material. The first edge of the elastic device is joined to the inelastic material, for instance, glued or welded to the inelastic material, optionally after having folded the second edge of the inelastic material around the first edge of the band-like elastic device so as to form from the mutually joined parts a stretchable, puckered first barrier edge. The second edge of the elastic device will be free and form a stretchable, essentially smooth second barrier edge. The barrier element is incorporated in an absorbent article, by fastening the first edge of said barrier element to the top liquid-permeable sheet of the article, close to the longitudinally extending edge, or to the bottom liquid-impermeable sheet at the edge part of said article, said barrier element being turned so that the free edge or part of said elastic device faces towards the longitudinal centre line of the article.

When manufacturing an inventive absorbent article, the first edge of the web-like essentially inelastic and essentially liquid-impermeable material may be fastened to the top liquid-permeable sheet of the article close to said longitudinally extending edge, or to the bottom liquid-impermeable sheet at the edge of the article prior to forming the puckered barrier edge in accordance with the afore going. The elastic device will suitably have a width of at least 0.5 cm, preferably at least 1.0 cm. The width of the elastic device is preferably smaller than 5 cm.

DETAILED DESCRIPTION OF THE INVENTION

The invention will now be described in more detail with reference to particular embodiments thereof and also with reference to the accompanying drawings, in which FIG. 1 illustrates a diaper that includes conventional liquid barriers;

FIGS. 2a, b and c illustrate the manner in which conventional liquid barriers and inventive liquid barriers are formed and fastened to the liquid-permeable top sheet or to the liquid-imperneable bottom sheet of an absorbent article; and FIGS. 3a and b illustrate respectively the manner in which an inventive liquid barrier and a conventional liquid barrier lies against the wearer of the article.

Figure 4A:
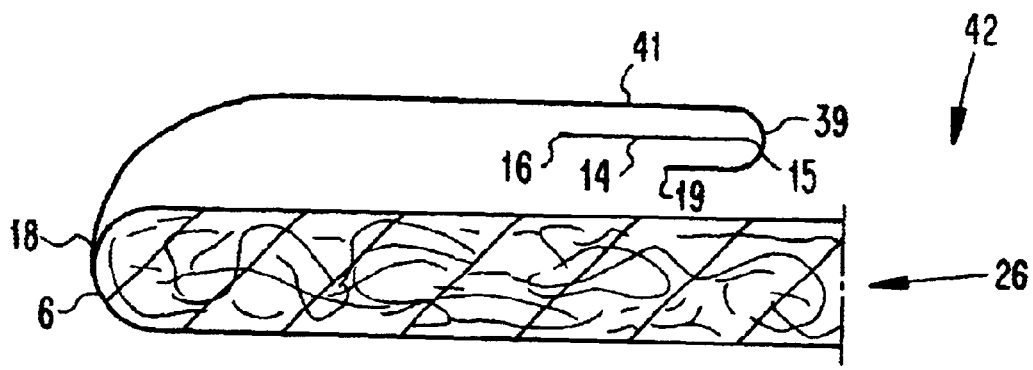
Figure 4B:
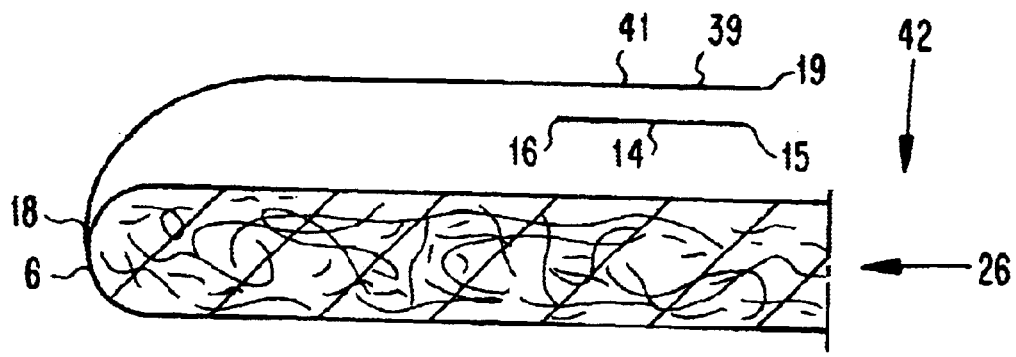

FIGS. 4a and 4b illustrate embodiments of an inventive absorbent article with a liquid-impermeable top sheet.

The barriers are illustrated schematically in the majority of the Figures, with the component layers mutually separated for the sake of clarity.

The outer barriers, the leg elastic 4, 5, are usually comprised of elastic threads which are fastened in a stretched state between the top liquid-permeable sheet and the bottom liquid-impermeable sheet of the absorbent article.

Figure 1:
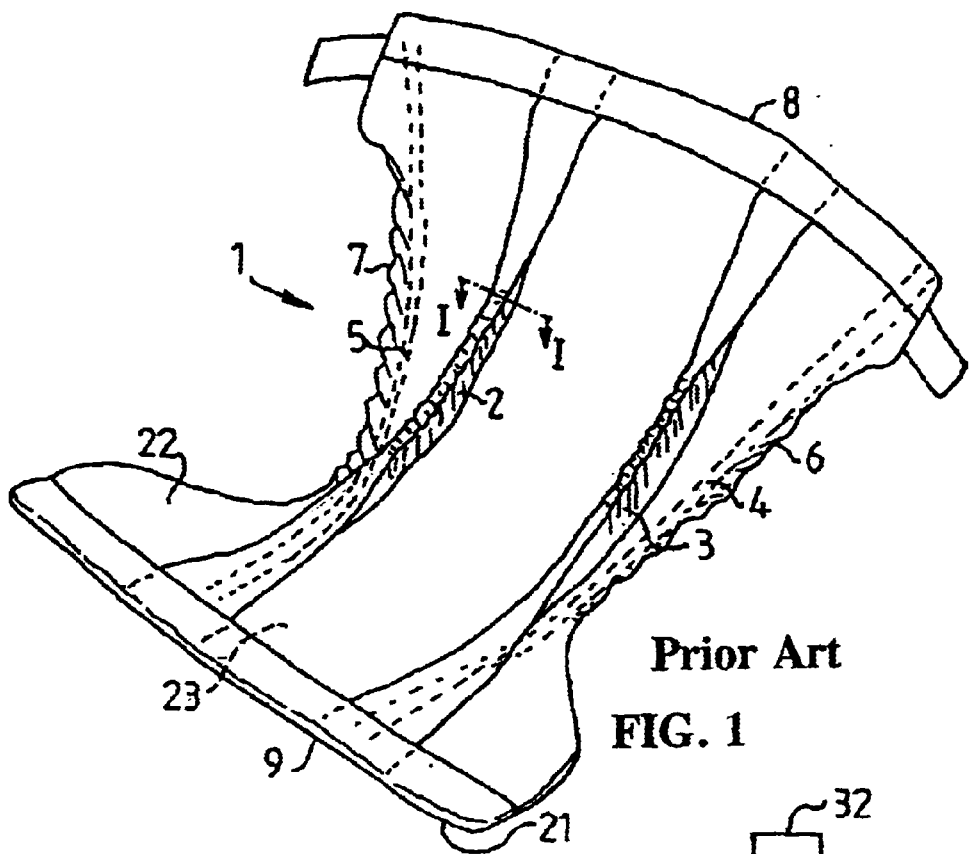
FIG. 1a is an enlarged cross-sectional view of a liquid barrier according to conventional practice, said view being taken on the line I—I in FIG. 1.
FIG. 1b is a cross-sectional view of one embodiment of an inventive liquid barrier, said view corresponding to an enlarged cross-sectional view taken on the line I—I in FIG. 1.
Figure 1A:
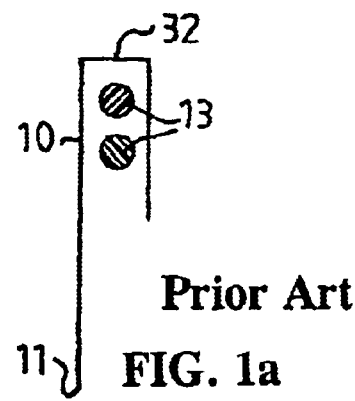

Each inner barrier 2,3 is comprised of an elongated element 10 made of an essentially liquid-impermeable material and fastened at one longitudinal edge 11 to the top liquid-permeable sheet 22 or to the bottom liquid-impermeable sheet 21 in the vicinity of the longitudinally extending edges 6,7. The other edge 12 of the element (FIG. 1a) is folded around a prestretched elastic thread or threads 13 and fastened to said threads such as to form a puckered barrier edge 32 which is intended to lie against the wearer when the article is donned. When the diaper is used, the liquid barrier 2,3 will lie against the crotch and buttocks of the wearer and should prevent the leakage of liquid in these areas.

In one embodiment, the leg elastic 4, 5 constitute the outer liquid barriers and the inner cuffs 2, 3 constitute inner liquid barriers. In another embodiment of the invention, the leg elastic is the sole liquid barriers 4, 5 and will thus constitute the inner liquid barriers.

Figure 1B:
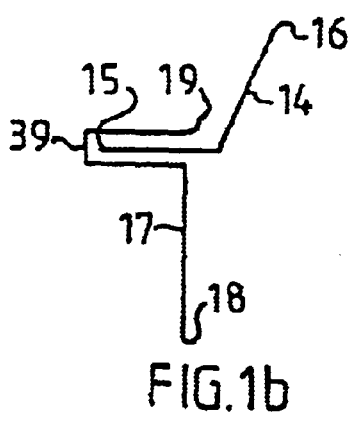

FIG. 1b illustrate a barrier element according to the invention. The barrier element includes an essentially inelastic, generally liquid-impermeable material sheet 17 having a free edge 18 which is intended to be fastened to an absorbent article, and another edge 19 which is folded around a first edge 15 of a band-like elastic element or elastic band 14. The first edge of the elastic band is inserted in a prestretched state into the channel that is formed by folding the other edge of the inelastic material sheet and the edge-parts are joined together, e.g. welded or glued together, such as to form a stretchable, puckered first barrier edge 39. The other, or second, edge 16 of the elastic element is free and forms a stretchable, essentially smooth second barrier edge which has an essentially smooth surface in both a relaxed and a tensioned state.

Figure 2B:
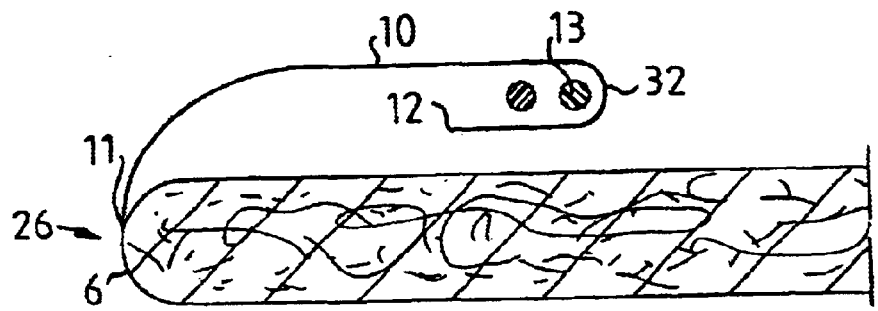
Figure 2B:
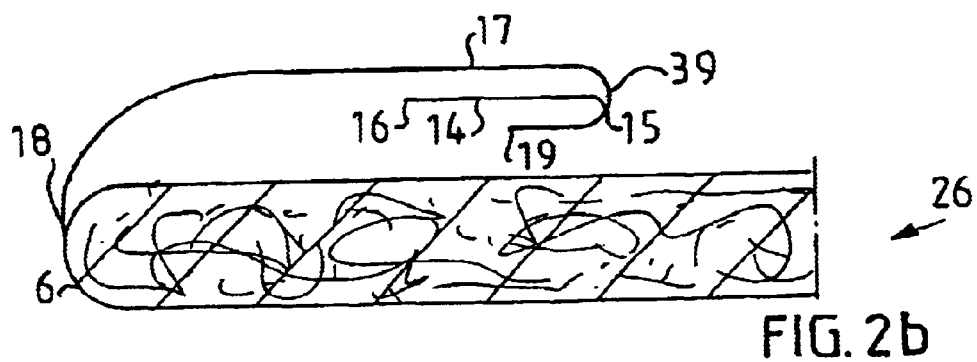

FIG. 2a illustrates schematically an enlarged liquid barrier constructed in accordance with conventional practice, while FIGS. 2b and c illustrate schematically two embodiments of an inventive liquid barrier. The Figures show how the liquid barriers are applied to the absorbent article.

Figure 2C:
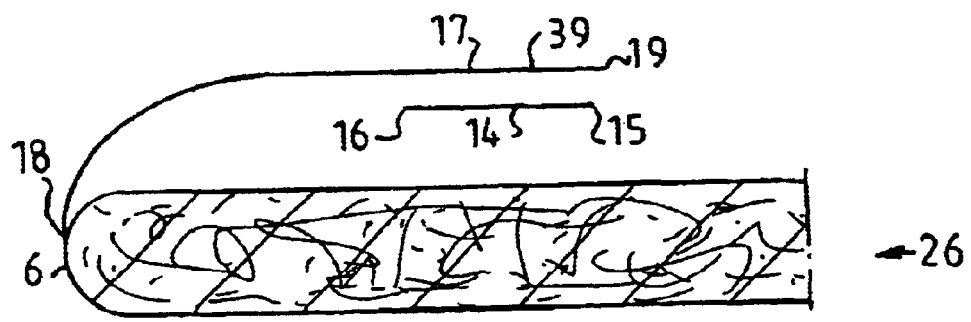

The conventional liquid barrier is fastened with the first edge 11 of the elongated element 10 to one of the sheets of the absorbent article, along its longitudinal edge 6. The other edge 12 of the elongated element 10 is folded in so as to form a channel in which an elastic thread or elastic threads 13 are fastened in a stretched state, e.g. glued. The element 10 is fastened to the nonwoven surface of the article, e.g. glued or welded thereto. The barrier edge formed by this channel will define the puckered barrier edge 32 and will lie against the wearer in use FIGS. 2b and c illustrate an inventive liquid barrier. An elongated, essentially inelastic and essentially liquid-impermeable material sheet 17 is fastened at its first edge 18 to the top or the bottom sheet of the absorbent article 26 along longitudinal edge 6 thereof. The first edge is fastened by gluing or welding the edge, for instance. An elongated elastic band device 14 having two longitudinal edges 15, 16 is fastened in a stretched state with its first edge 15 against the elongated, essentially inelastic and liquid-impermeable material sheet 17. In the case of the FIG. 2b embodiment, the elastic device 14 is fastened in the inwardly folded second edge 19 of the essentially inelastic sheet 17, with the inwardly folded edge facing down towards the absorbent article. In the case of the FIG. 2c embodiment, the elastic device 14 and the liquid-impermeable sheet 17 lie against one another without folding the second edge 19 of the sheet. In this case, the edges of bother sheets are fastened together, so as to form a puckered first barrier edge 39. In order to form the puckered edge, the joint is given a certain width that corresponds to the desired edge width, or the sheets are fastened slightly inwards of the edges 15, 19.

The elastic device is secured with glue or a weld, for instance. The second edge 16 of the elastic device will be free and form a longitudinally extending free part of the elastic device. The elastic will lie inwardly folded and protected beneath the elongated, essentially inelastic material during manufacture and packaging.

The free edge 16 of the elastic device presents an essentially smooth surface both in a relaxed and in a stretched state and is intended to provide a "seal" at the contact surface between the wearer's skin and the liquid barrier when the absorbent article is donned.

FIG. 1b shows the inventive liquid barrier as it will appear when used in an absorbent article. When the absorbent article is unfolded for use, the elastic device 14 will be "folded up" from the upper surface of the article. When the absorbent article is stretched in a direction towards its transverse edges 8, 9, the free edge 16 of the elastic device will face inwards towards the centre of the absorbent article, so as to be as short as possible. The more the article is stretched, the closer the edge 16 will approach the absorbent article. The elastic device will lie generally parallel to the surface of the absorbent article. When tension on the liquid barrier is relieved, the free part of the elastic, i.e. the edge 16, will endeavor to follow the shortest route, and will therewith strive to move upwards, as evident from FIG. 1b. This takes place when the absorbent article, e.g. a diaper, is donned by the user. The liquid barrier will relax as the article is folded around the wearer's crotch, and the free edge 16 of the elastic will strive to move upwards.

FIG. 3a illustrates the elastic device 14 in abutment with the wearer's skin. The essentially smooth surface of the elastic device provides a better seal, and hence no pores will occur between the barrier edge and the skin. The barrier edge also provides an effective "seal" against the wearer's skin, because liquid that flows out in the space between the absorbent body of the article and the wearer's skin will press the barrier edge against the wearer's skin.

FIG. 3b is a corresponding view of a conventional liquid barrier. In this case, through-penetrating pores exist between the wearer's skin and the puckered barrier edge 32. Furthermore, liquid present in the space between the absorbent body and the wearer's skin will press the barrier edge outwards. This article will therefore leak much earlier than the inventive article.

In another embodiment, transverse barriers are fastened to respective transverse edges 8, 9 of the absorbent product.

FIGS. 4a and 4b illustrate embodiments of an inventive absorbent article with a liquid-impermeable top sheet 41. An aperture 42 is intended to lie in register with the anus and urethral orifice of the wearer. The liquid-impermeable top sheet 41 is provided with a stretchable sealing edge puckered by means of a prestretched elastic band 14 disposed in the essentially liquid-impermeable sheet around the aperture. When the article is donned, the elastic band 14 will lie against the wearer with a free part of the elastic band facing inwards toward the aperture and a puckered barrier edge facing outwards from the aperture.

The essentially inelastic material may be a nonwoven material, e.g. a multi-layer nonwoven material. This material may be an SMS material, i.e. spunbond-meltblown-spunbond.

The material in the elastic device may be elastic film based on styrene block copolymers, such as SBS (styrene-butadien-styrene), SIS (styrene-isoprene-styrene), SEBS (styrene-ethylene-butylene-styrene) or SEPS (styrene-ethylene-propylenestyrene). The film may also consist of several layers. For instance, it may be a three-ply film of which the outer layers consist of polypropylene, where the polypropylene is intended to facilitate the arrangement of the film on the inelastic material or on the absorbent article. The polypropylene may, for instance, facilitate gluing to the other materials. Polypropylene also gives a more comfortable feeling to the skin than a number of other elastic films, which can feel like plastic against the skin, which one wishes to avoid.

It will be understood that the invention is not restricted to the afore described and illustrated exemplifing embodiments thereof and modifications can be made within the scope of the invention as defamed in the following Claims.

What is claimed is:

1. An absorbent article that includes:
   longitudinally extending extremities;
   transversely extending extremities;
   a liquid-permeable upper sheet intended to lie proximal to a wearer in use;
   a liquid impermeable bottom sheet intended to lie distal from a wearer in use;
   an absorbent body disposed between the liquid-impermeable bottom sheet and the liquid-permeable upper sheet; and
   at least one longitudinally extending liquid barrier on each side of a longitudinal center line of the upper sheet, each said liquid barrier comprising:

an elongated, prestretched elastic band having a first elastic edge and a second elastic edge, an elongated, essentially liquid-impermeable and inelastic material having first and second longitudinal inelastic edges, where the first inelastic edge is fastened to the bottom or upper sheet along or adjacent to the longitudinal extremities, and the second longitudinal inelastic edge is fastened to the first elastic edge of the elongated, prestretched elastic band such as to form a stretchable, puckered first sealing edge and a longitudinal free part of the elastic band constituting a stretchable, essentially smooth second sealing edge, the first and second sealing edges being intended to lie against the wearer when the absorbent article is donned, with said longitudinal free part facing towards the longitudinal center line and the stretchable, puckered first sealing edge facing outwards from the longitudinal center line.

2. An absorbent article according to claim 1, wherein said free part is formed by said second elastic edge.

3. An absorbent article according to claim 1, wherein said band-like elastic device is bent longitudinally to form a bent part; and said first and second elastic edges are fastened to the second inelastic edge, said bent part constituting said free part.

4. An absorbent article according to claim 1, wherein the second inelastic edge is folded inwards towards the center line of the article so as to form a channel around said first elastic edge, where said first elastic edge is fastened.

5. An absorbent article according to claim 1, wherein said elastic band is comprised of an elastic film.

6. An absorbent article according to claim 5, wherein said elastic film is styrene-butadiene-styrene, styrene-isoprene-styrene, styrene-ethylene-butylene-styrene or styrene-ethylene-propylene-styrene.

7. An absorbent article according to claim 1, wherein said absorbent article is a diaper, a sanitary napkin or an incontinence guard.

8. A web-like element intended for use as a liquid barrier in an absorbent article, where the element comprises:

an elongated, prestretched elastic band;

an elongated, essentially liquid-impermeable and inelastic material having first and second longitudinally extending inelastic edges, where the first inelastic edge is free and intended to be fastened to the absorbent article, and the second inelastic edge is fastened to the elongated, prestretched elastic element such as to form a stretchable, puckered sealing edge, wherein the elastic band has first and second longitudinal elastic edges, where at least said first elastic edge is fastened in a prestretched state to the second inelastic edge so that the fastened first elastic edge and the second inelastic edge constitute the stretchable, puckered sealing edge;

and the elastic band comprises a longitudinally extending free part which constitutes a stretchable, essentially smooth second sealing edge intended to lie against a wearer.

9. An element according to claim 8, wherein said free part is formed by said second elastic edge.

10. An element according to claim 8, wherein said band-like elastic device is folded lengthwise to form a folded part; and said first and second elastic edges are fastened to the second inelastic edge, said folded part constituting said free part.

11. An element according to claim 8, wherein the second inelastic edge is folded inwards so as to form a channel around said first elastic edge, where said first elastic edge is fastened.

12. An element according to claim 11, wherein said first elastic edge is fastened in said channel by gluing or welding.

13. An element according to claim 8, wherein the essentially inelastic material is comprised of a nonwoven material.

14. An element according to claim 13, wherein said essentially inelastic material comprises a multi-layer nonwoven material.

15. An element according to claim 8, wherein said elastic device has a width of at least 0.5 cm.

16. An element according to claim 15, wherein said elastic device has a width of at least 1.0 cm.

17. An element according to claim 8, wherein said elastic device has a width of at least 1.0 cm.

18. An absorbent article comprising:

longitudinally extending extremities;

transversely extending extremities;

a liquid-permeable upper sheet intended to lie proximal to a wearer in use;

a liquid impermeable bottom sheet intended to lie distal from the wearer in use;

an absorbent body disposed between the liquid-impermeable bottom sheet and the liquid-permeable upper sheet;

a liquid impermeable top sheet at a side of the upper sheet opposite the absorbent body intended to lie against a wearer, said liquid impermeable top sheet having
at least one edge defining at least one aperture intended to lie in register with an anus and an urethral orifice of the wearer and
an elastic element for shaping the absorbent article against the wearer; and an elastic band comprising first and second longitudinal elastic edges, said first elastic edge being fastened in a prestretched state to an edge of the top sheet such that said first elastic edge and said top sheet edge form a stretchable, puckered first sealing edge, the elastic band comprising a free, stretchable, essentially smooth, second sealing edge, wherein said elastic band is fastened to the top sheet in a manner that when the absorbent article is donned, the elastic band lies against the wearer, the free, stretchable, essentially smooth, second sealing edge faces toward the at least one aperture, and the stretchable, puckered first sealing edge faces outward from the at least one aperture.

19. An absorbent article according to claim 18, wherein said elastic band is comprised of an elastic film.

* * * * *